United States Patent
Markovich

(10) Patent No.: US 11,583,599 B1
(45) Date of Patent: Feb. 21, 2023

(54) MENU SANITIZING MACHINE

(71) Applicant: Michael Markovich, New Smyrna Beach, FL (US)

(72) Inventor: Michael Markovich, New Smyrna Beach, FL (US)

(*) Notice: Subject to any disclaimer, the term of this patent is extended or adjusted under 35 U.S.C. 154(b) by 290 days.

(21) Appl. No.: 17/094,488

(22) Filed: Nov. 10, 2020

(51) Int. Cl.
*A61L 2/10* (2006.01)

(52) U.S. Cl.
CPC ........... *A61L 2/10* (2013.01); *A61L 2202/122* (2013.01); *A61L 2202/20* (2013.01)

(58) Field of Classification Search
CPC .. A61L 2/10; A61L 2202/122; A61K 2202/20
USPC ............................ 250/453.11, 454.11, 455.11
See application file for complete search history.

(56) References Cited

U.S. PATENT DOCUMENTS

| 2,253,251 | A | 8/1941 | Selig | |
| 9,415,124 | B2 | 8/2016 | Beak | |
| 2022/0092947 | A1* | 3/2022 | Steadman | A61L 2/10 |

* cited by examiner

*Primary Examiner* — Nicole M Ippolito
(74) *Attorney, Agent, or Firm* — Sanchelima & Associates, P.A.; Christian Sanchelima; Jesus Sanchelima

(57) ABSTRACT

A system for a sanitizing machine including a housing assembly and a sterilizing assembly is disclosed. The housing assembly includes a housing with a feeding tray and a catch tray attached. The housing assembly further includes rollers within. Importantly, the sterilizing assembly including ultraviolet lights are secured within the housing. The ultraviolet lights are used to cleanse and sanitize menus that get inserted into the housing with radiation. The menus are received on the feeding tray, then the menus are inserted into the housing in which the ultraviolet lights eliminate germs, diseases or viruses from the surface of the menus. Once the menus are completely sanitized, the menus exit housing and are received on the catch tray ready for usage again. Sanitation of the menus is done without the use of harsh chemicals.

19 Claims, 3 Drawing Sheets

MENU SANITIZING MACHINE

BACKGROUND OF THE INVENTION

1. Field of the Invention

The present invention relates to a sanitizing machine, more particularly, to a sanitizing machine that helps to automatically cleanse and sanitize restaurant menus after usage.

2. Description of the Related Art

Several designs for sanitizing have been designed in the past. None of them, however, include a machine for sterilizing restaurant menus using UV-C light wherein the machine resembles a document scanner comprising a conveyor wherein the menu is placed on the conveyor which advances the menu through an enclosure which exposes the menu to a UV-C light which kills any bacteria and viruses on the surface.

Applicant believes that a related reference corresponds to U.S. Pat. No. 9,415,124 for a pass through paper object sanitizing device which uses UV lights. Applicant believes that another related reference refers to U.S. Pat. No. 2,253,251 for a cabinet for storing and sterilizing objects using a UV light. None of these references, however, teach of a sanitizing machine which automatically sanitizes restaurant menus with a UV-C light after usage as the restaurant menus are pass through the sanitizing machine.

Other documents describing the closest subject matter provide for a number of more or less complicated features that fail to solve the problem in an efficient and economical way. None of these patents suggest the novel features of the present invention.

SUMMARY OF THE INVENTION

It is one of the objects of the present invention to provide a sanitizing machine which helps to cleanse and sanitize restaurant menus after usage.

It is another object of this invention to provide a sanitizing machine which helps to increase the health and safety of users.

It is still another object of the present invention to provide a sanitizing machine which helps to reduce the cross contamination of germs, viruses or diseases between people.

It is also another object of the present invention to provide a sanitizing machine that expedites the cleaning and sanitizing process for restaurant menus.

It is another object of the present invention to provide a sanitizing machine that sanitizes without the use of chemicals or liquids.

It is yet another object of this invention to provide such a device that is inexpensive to implement and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

Figure 1:
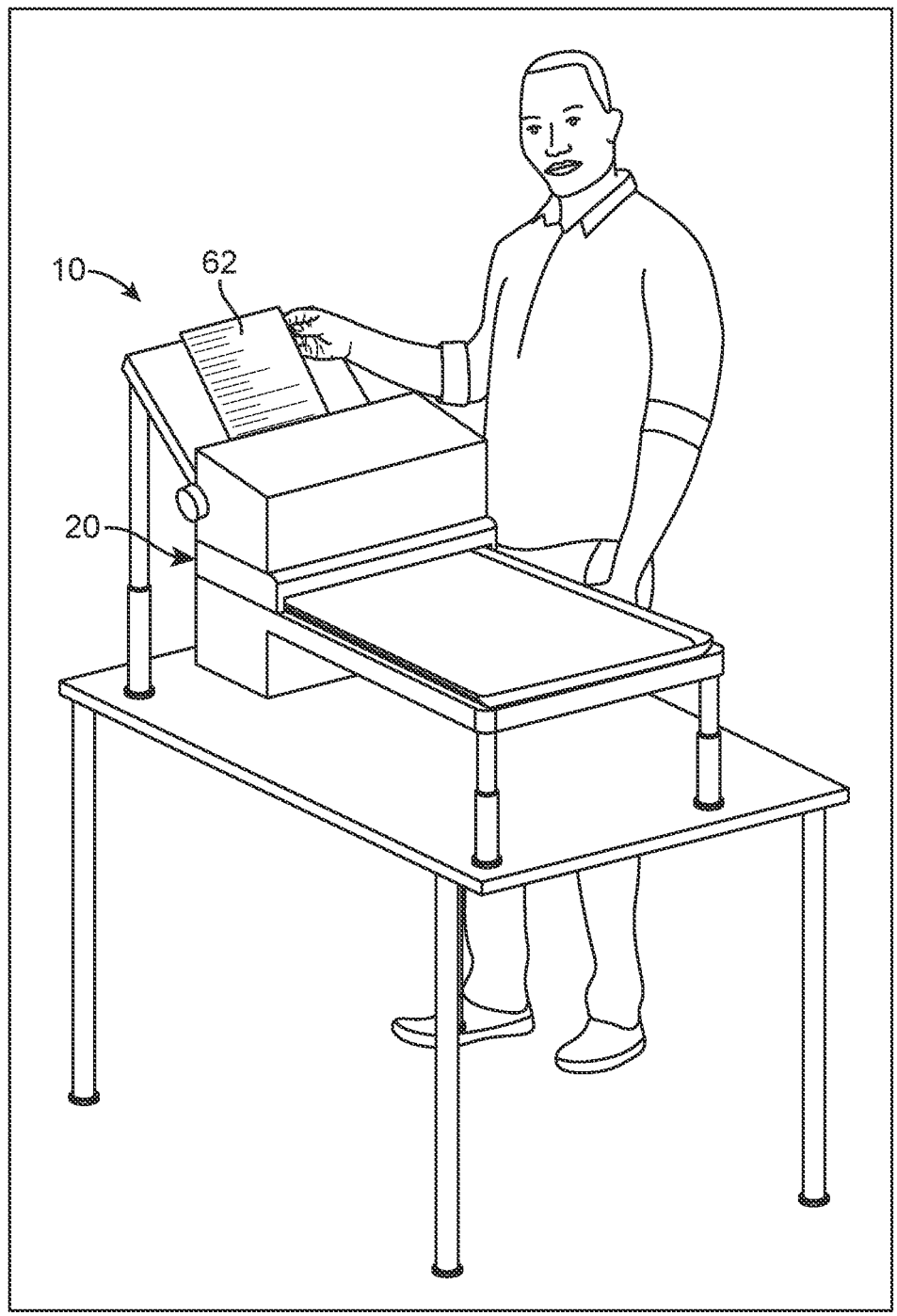
FIG. 1 represents an operational view of menus 62 being sanitized with sanitizing machine 10.

Referring now to the drawings, where the present invention is generally referred to with numeral 10, it can be observed that it, a sanitizing machine 10, basically includes a housing assembly 20 and a sterilizing assembly 40.

Sanitizing machine 10 may help to facilitate and expediate the process of cleansing and sanitizing menus 62. Sanitizing machine 10 helps to eliminate viruses, diseases or germs on the surface of menus 62. Thereby helping to reduce the chance of cross contamination between people that come into contact with menus 62 of various different restaurants or establishments. Resulting in the health and safety of people such as workers and customers to be increased. Additionally, sanitizing machine 10 helps to automatically sanitize menus 62 reducing the amount of contact necessary with dirty menus 62. Advantageously, sanitizing machine 10 cleans and sterilizes menus 62 without the use of harsh chemicals.

Figure 2:
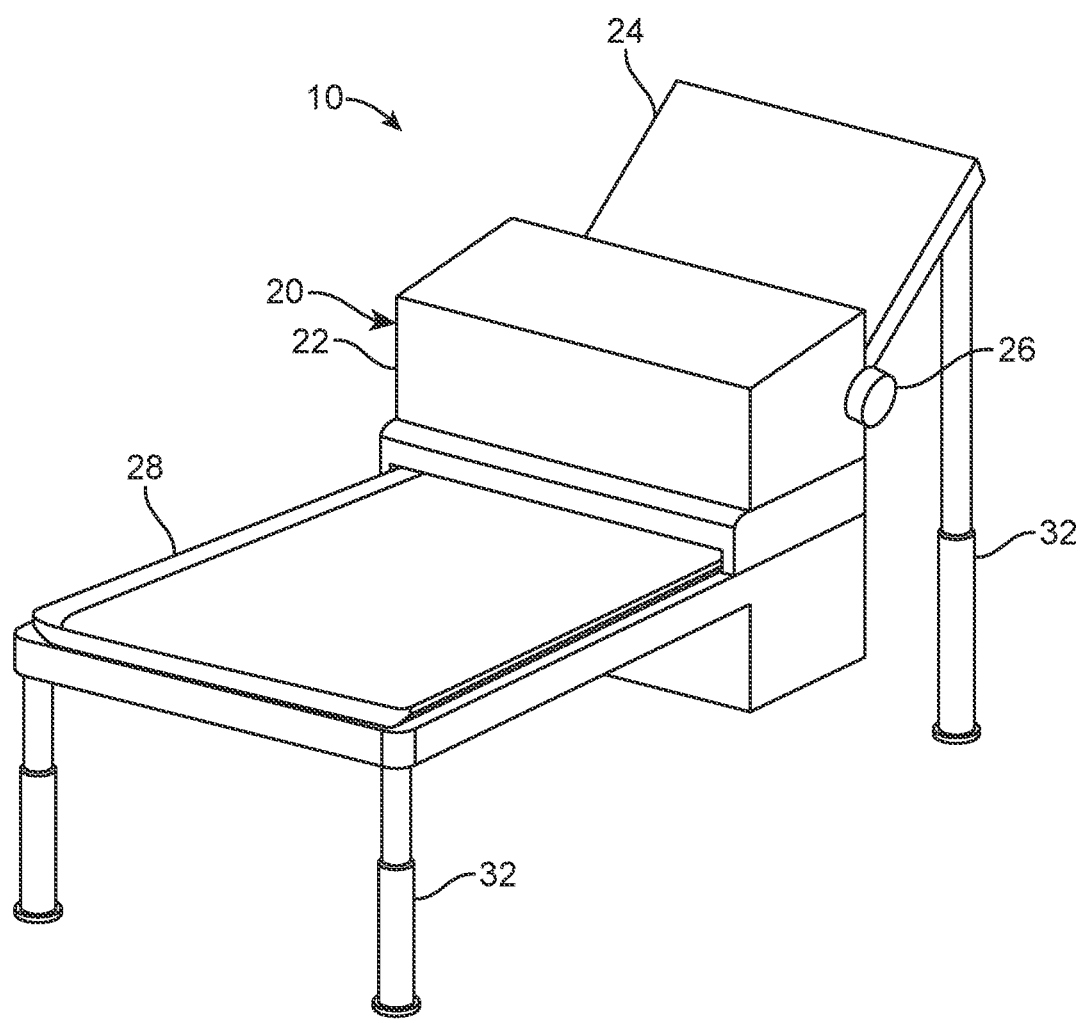
FIG. 2 shows an isometric view of sanitizing machine 10.
Figure 3:
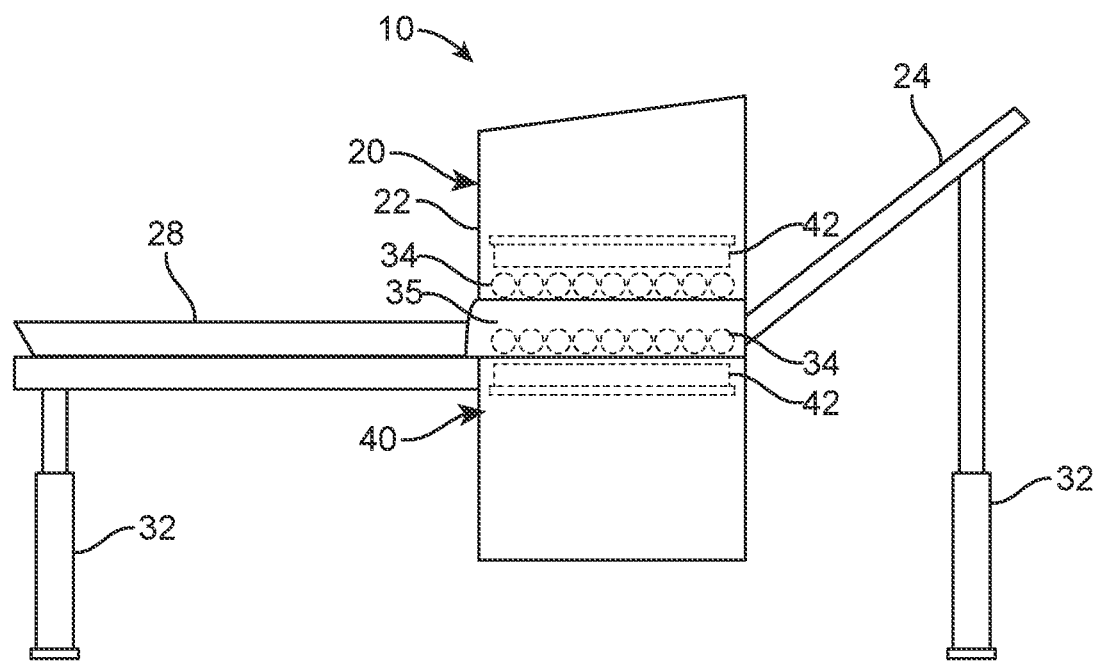
FIG. 3 illustrates a see through side view of sanitizing machine 10 showing sterilizing assembly 40 within housing 22.

As best illustrated in FIGS. 1-3, sanitizing machine 10 may include a housing assembly 20. It is to be understood that within housing assembly 20 may be enclosed sterilizing assembly 40. Housing assembly 20 may include a housing 22 through which menus 62 are advanced through for sanitation thereof. It is to be understood housing 22 may alternatively be referred to as an enclosure. Housing 22 may have a rectangular shape, in one embodiment. It is to be understood that housing 22 may have a width that can accommodate various different sized menus 62 being fed therethrough. It may be suitable for housing 22 to be made of materials such as plastic, aluminum, wood or the like to remain lightweight. Housing 22 may preferably be rigid to adequately protect the components of the present invention within.

Secured to one side of housing 22 may be a feeding tray 24. It is to be understood that feeding tray 24 may be in constant abutting contact with housing 22. Feeding tray 24 may receive menus 62 needing to be sanitized. It may be suitable for feeding tray 24 to be rectangular and oversized to accommodate various sized of menus 62 thereon. Feeding tray 24 may be movable and positioned at different angles relative to housing 22. Preferably, feeding tray 24 may be angled or sloped downwardly towards housing 22 during usage. The angled positioning of feeding tray 24 may help to feed menus 62 into housing 22 with the assistance of gravity. Menus 62 may enter housing 22 from feeding tray 24 through a first housing opening. When feeding tray 24 is not angled sufficiently for gravity to feed menus 62 into housing, menus 62 may be pushed into housing 22 manually. Feeding tray 24 may have a range of possible positions starting from being flat and perpendicular to housing 22 and creating a right angle with housing 22 to being angled against housing 22 and creating an acute angle with housing 22. It may be necessary to angle feeding tray 24 to help accommodate different sized menus 62 to be fed into housing 22. Larger or thicker menus 62 may require for feeding tray 24 to be flat to be fed into housing 22. Smaller or thinner menus 62 may require for feeding tray 24 to be angled to be fed into housing 22.

A knob 26 may be secured in abutting contact between housing 22 and feeding tray 24 to help position feeding tray 24 as desired. Knob 26 may be actuated through rotation. Turning of knob 26 towards feeding tray 24 may lower feeding tray 24. Turning of knob 26 towards housing 22 may raise and angle feeding tray 24. Knob 26 may extend outwardly and away from housing 22 and feeding tray 24. In one embodiment, knob 26 may be circular with grips extending about a perimeter thereof.

Mounted to housing 22, opposite to feeding tray 24, may be a catch tray 28. Catch tray 28 may be similarly shaped and sized to feeding tray 24. It may be suitable for catch tray 28 to be rectangular and oversized to accommodate various sized of menus 62 thereon. Catch tray 28 may gather menus 62 exiting housing 22 after being sanitized. Menus 62 may exit housing 22 through a second housing opening. Catch tray 28 may preferably be made of similar materials as feeding tray 24. Catch tray 28 may be perpendicular to housing 22 and preferably remain stationary.

Optionally, underneath of feeding tray 24 and catch tray 28 may be legs 32. Legs 32 may extend downwardly towards a surface to provide stability and support to feeding tray 24 and catch tray 28. It may be suitable for legs 32 to be telescopic to allow adjustments in height as needed. It is to be understood that legs 32 may be set to different heights depending on positioning of feeding tray 24.

Within housing 22 may be secured rollers 34, as best seen in FIG. 3. Rollers 34 may spin or rotate to help to guide menus 62 through housing 22 from feeding tray 24 to catch tray 28 for sanitation. Rollers 34 may line the top and bottom of housing 22. Thereby creating a channel 35 in between rollers 34 for menus 62 to be guided through within housing 22. It is to be understood that within housing 22, rollers 34 may make direct contact with menus 62 to be able to usher menus 62 through housing 22. Rollers 34 may preferably line an entire length of housing 22 to allow for the transportation of menus from feeding tray 24 to catch tray 28 be quick and efficient. It is to be understood that rollers 34 may be adjacent and parallel to each other within housing 22. It is to be understood that rollers 34 may alternatively be a conveyor belt, in one embodiment.

Housing 22 may include controls 36. Controls 36 may help to control the function and operation of sanitizing machine 10. One of controls 36 may be used to power sanitizing machine 10 on and off. Another of controls 36 may be actuated to active and deactivate rollers 34. Yet another of controls 36 may be actuated to activate or deactivate sterilizing assembly 40 as needed. It may also be suitable to control the intensity of sterilizing assembly 40 with controls 36. It is to be understood that controls 36 may be buttons or switches. Controls 36 may preferably be located on housing 22 and be adjacent to each other. It is to be understood that controls 36 may be switches or buttons.

Attached to housing 22 may be a power cord 38. Power cord 38 may help to connect sanitizing machine 10 to a power source. Thereby allowing for sanitizing machine 10, rollers 34, sterilizing assembly 40 and all other electrical components be powered with sufficient energy for proper functioning and operation thereof. It may be suitable for the sanitizing machine 10 to include replaceable or rechargeable batteries to power all electrical components of sanitizing machine 10.

Enclosed within housing 22 may be sterilizing assembly 40. Sterilizing assembly 40 may help to sanitize and clean menus 62 being advanced into housing 22. Importantly, sterilizing assembly 40 may include ultraviolet (UV) lights 42. UV lights 42 may be secured within housing 22 as best depicted in FIG. 3. UV lights 42 may be secured to a top portion and a bottom portion of housing 22. It may be suitable for UV lights 42 to be parallel and adjacent to rollers 34. UV lights 42 sanitize menus 62 inserted into housing 22 by exposing the menus 62 to radiation emitted from UV lights 42. UV lights 42 eliminate diseases and viruses located on the surface of menus 62. UV lights 42 help to eliminate the need to sanitize menus 62 with harsh chemicals. Preferably, UV lights 42 may be UV-C lights. However, it may also be suitable for UV lights 42 to be one of UV-A or UV-B lights.

Figure 4:
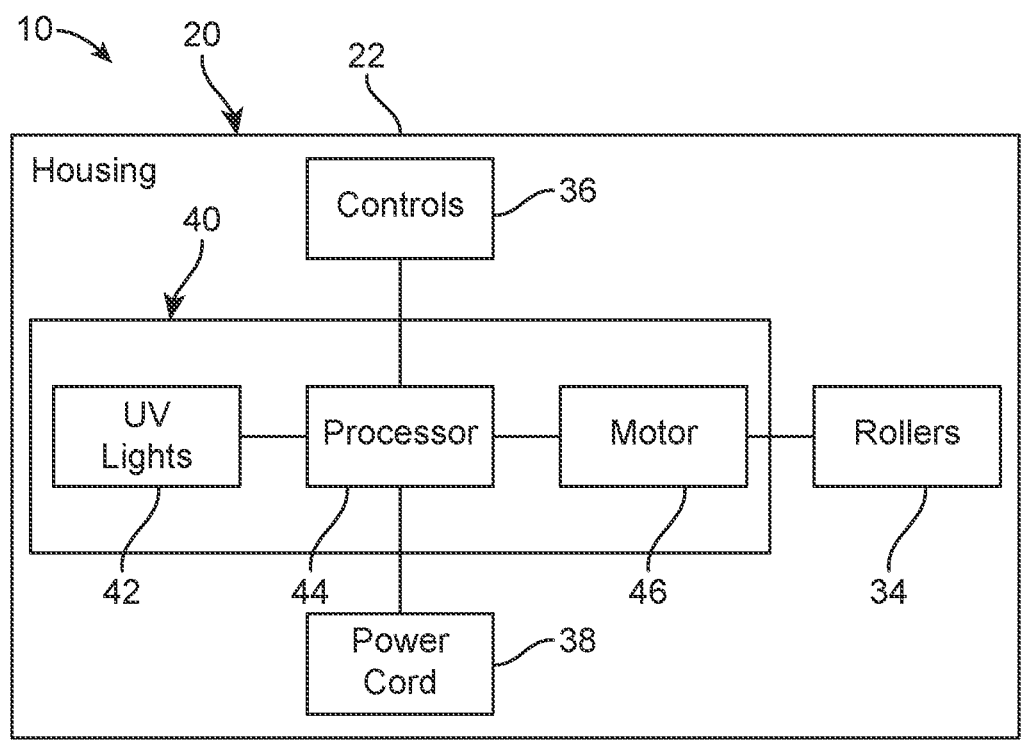
FIG. 4 is a representation of a chart of sanitizing machine 10.

Sterilizing assembly 40 may further include a processor 44 and a motor 46, as best illustrated in FIG. 4. Processor 44 may be interconnected to controls 36, power cord 38, UV lights 42, and motor 46 to allow for proper function of sanitizing machine 10. Processor 44 may help to determine when controls 36 are actuated to actuate the component that corresponds with the actuated of controls 36. Processor 44 may help to provide proper energy to the needed components from the selected power source. It is to be understood that motor 46 may be connected to rollers 34 to cause rollers 34 to rotate when needed. Processor 44 may help motor 46 to determined when it is time to turn on. Processor 44 may also help UV lights 42 to determined when to turn on after the corresponding of controls 36 is actuated. Processor 44 may help to control the radiation intensity of UV lights 42.

Sanitizing machine 10 helps to eliminate the need to sanitize menus 62 to eliminate germs, diseases or viruses that may be on the surface of menus 62. Advantageously, sanitation of menus 62 is done without chemicals with the present invention. In one embodiment, sanitizing machine 10 may have a small front print such that it can be placed on a countertop. Sanitizing machine 10 helps to improve the health and safety of people that may come in contact with menus 62 which are continuously being handled by various people daily.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A system for a sanitizing device, comprising:
  a) a housing assembly including a housing;
  b) a sterilizing assembly including ultraviolet lights emitting radiation, said ultraviolet lights secured within said housing;
  c) menus, said menus being inserted into said housing to expose said menus to the ultraviolet lights to eliminate germs, viruses or bacteria on a surface of said menus for sanitation thereof and
  d) attached to said housing is a feeding tray leading to an interior of said housing, said menus needing sanitation received on said feeding tray.

2. The system of claim 1, wherein said feeding tray is in constant abutting contact with said housing.

3. The system of claim 1, wherein said feeding tray is movable at a predetermined angle with a knob, said knob being rotated to adjust the angle of said feeding tray with respect to said housing.

4. The system of claim 3, wherein said knob is rotated towards said feeding tray to lower said feeding tray, said knob is rotated towards said housing to raise said feeding tray.

5. The system of claim 1, wherein attached to said housing opposite of said feeding tray is a catch tray, said catch tray receiving said menus exiting from said housing.

6. The system of claim 5, wherein said catch tray is stationary and perpendicular to said housing.

7. The system of claim 5, wherein underneath each of said feeding tray and said catch tray are legs to provide support to said feeding tray and said catch tray.

8. The system of claim 7, wherein said legs are telescopic and adjustable in height.

9. The system of claim 1, wherein within said housing are rollers evenly spaced apart, said rollers advancing said menus through said housing.

10. The system of claim 9, wherein said rollers line a top portion and bottom portion of said housing, being parallel to each other.

11. The system of claim 10, wherein a channel is defined between said rollers along said top portion and said bottom portion, said menus advancing within said housing along said channel.

12. The system of claim 11, wherein said ultraviolet lights emit radiation into said channel, from above and below of said channel, to sanitize said menus within said channel from a top and a bottom simultaneously.

13. The system of claim 10, wherein said housing includes controls for controlling and actuating of said system.

14. The system of claim 13, wherein said controls are buttons or switches.

15. The system of claim 9, wherein said rollers are a conveyor.

16. The system of claim 9, wherein attached to said rollers is a motor for actuation of said rollers.

17. The system of claim 1, wherein said housing includes a power cord for powering of said housing assembly and said sterilizing assembly.

18. The system of claim 1, wherein a processor is included.

19. A system for a sanitizing device, comprising:
a) a housing assembly including a housing, said housing including a feeding tray on one end, said feeding tray being movable with a knob attached thereto, said knob being rotated to raise and lower said feeding tray as desired, a catch tray secured to said housing at an opposite end of said feeding tray, said housing further including rollers within, a channel defined within said housing between said rollers;
b) a sterilizing assembly including ultraviolet lights emitting radiation, said ultraviolet lights secured within said housing, said ultraviolet lights emitting radiation to said channel;
c) menus, said menus received on said feeding tray, said menus being inserted into said housing and advancing through said housing with said rollers, said menus exposed to the ultraviolet lights to eliminate germs, viruses or bacteria on a top surface and a bottom surface of said menus simultaneously.

* * * * *